United States Patent [19]
Da Rold

[11] Patent Number: 5,968,049
[45] Date of Patent: Oct. 19, 1999

[54] MILLING CUTTER FOR MEDICAL PURPOSES

[75] Inventor: Orlando Da Rold, Solothurn, Switzerland

[73] Assignee: Precifar S.A., Orvin, Switzerland

[21] Appl. No.: 09/065,896

[22] Filed: Apr. 23, 1998

[30]     Foreign Application Priority Data

May 22, 1997 [CH]   Switzerland ........................... 1196/97

[51] Int. Cl.⁶ .................................................. A61B 17/16
[52] U.S. Cl. ............................................................ 606/80
[58] Field of Search .............................. 606/85, 84, 81, 606/80, 79, 86

[56]           References Cited

U.S. PATENT DOCUMENTS

| | | |
|---|---|---|
| 4,116,200 | 9/1978 | Braun et al. ................................ 606/81 |
| 4,811,632 | 3/1989 | Salyes . |
| 5,019,082 | 5/1991 | Frey et al. ................................. 606/85 |
| 5,100,267 | 3/1992 | Salyes . |
| 5,116,165 | 5/1992 | Salyes . |
| 5,203,653 | 4/1993 | Kudla . |
| 5,295,992 | 3/1994 | Cameron . |
| 5,376,092 | 12/1994 | Hein et al. ................................. 606/81 |
| 5,681,315 | 10/1997 | Szabo ........................................ 606/85 |
| 5,755,719 | 5/1998 | Frieze et al. .............................. 606/81 |

FOREIGN PATENT DOCUMENTS

0714634A1  11/1994  European Pat. Off. .

*Primary Examiner*—Michael Buiz
*Assistant Examiner*—David O. Reip
*Attorney, Agent, or Firm*—Bugnion S.A.; John Moetteli

[57]              ABSTRACT

Milling cutter for medical purposes, in particular for use in orthopedic operations, which has a milling body made of thin-walled material. The milling cutter may take various forms and is provided on its surface with a number of milling teeth which are arranged systematically in terms of number and position. The arrangement and shape of the milling teeth are precisely defined. As a result, the milling cutter is an accurate tool which not only facilitates the work of the surgeon but also considerably enhances the quality of intervention which can be achieved.

9 Claims, 3 Drawing Sheets

MILLING CUTTER FOR MEDICAL PURPOSES

FIELD OF THE INVENTION

The present invention relates to a milling cutter for medical purposes, in particular for use in orthopedic operations, which has a milling body made of thin-walled material, is shaped in accordance with the intended application and on its surface has milling teeth systematically assigned in terms of number and position to the milling cutter size and milling cutter shape, the arrangement and shape of the milling teeth being defined with the level of accuracy which is industrially conventional.

PRIOR ART

Milling cutters, or grating milling cutters, of the type mentioned above are known per se. They are also referred to as "forming reamer or reamer". In the field of surgery, such tools are used primarily for orthopedic operations. They are used to mill out the bone in the correct shape, i.e. to prepare an actual implant seat, so that an implant to be positioned is held as securely as possible. A very wide variety of milling cutters are used for this purpose, and their shape is determined by the particular application purpose.

A reamer as used, for example, for insertion in hip-joint sockets, is proposed, for example, by WO 95/1379. A very wide spread shape of the milling teeth is proposed, for example, in EP 0733 343. Acetabular reamers for hip-joint sockets with milling teeth as proposed in the abovementioned publication are generally produced by the following method: the positions of the milling teeth are drawn on to a metal disk of the appropriate thickness. This disk is then given the desired shape, for example by deep-drawing or pressing. In the next operation on the three-dimensional blank, an opening is stamped at each of the points which were drawn on beforehand. This opening is countersunk, in order to produce a cutting edge. Then, the opening is pressed open using a mandrel, so as to obtain the desired shape of a milling tooth with cutter and tooth pit.

After deep-drawing or pressing, the milling body has a three-dimensional shape, making it extremely complex to produce the teeth on conventional machine tools. The investment and outlay on setting the tools is out of all proportion to the output produced. For this reason, the operations of stamping, countersinking and pressing open using a mandrel are generally carried out by hand. Consequently, the quality is typical of manual labor. The openings for the milling teeth are stamped as seen in the region of the positions previously drawn on. It is therefore impossible for anyone to guarantee the accuracy of the dimensions of milling tooth and tooth pit after the stamping, countersinking and pressing-open operations. Every milling cutter produced in this way is a one-off component.

The conventional production processes are also notable for the fact that considerable scrap has to be thrown out during production. The shapes of the milling cutters and the milling teeth exhibit considerable inaccuracies. Moreover, the milling teeth are generally blunt, so that the surgeon has to use force in order to achieve the desired shape and dimensional accuracy in the bone region to be treated. Owing to the inaccuracy in the shapes of milling cutter and milling teeth, two milling cutters of the same dimension will produce different implant seats in the bone material. It depends on the skill of the surgeon and the quality of the milling cutter used whether the prepared implant seat in the bone material has the right size and shape for receiving the implant.

However, it would be desirable if the surgeon, by selecting the correct milling cutter, could be sure that the implant seat to be milled in the bone material would accommodate the industrially produced implant with as close a form fit as possible.

SUMMARY OF THE INVENTION

The object of the present invention is therefore to find a form of the milling tooth which allows a milling cutter of the type specified at the outset to be improved in such a way that milling cutter and milling teeth can be produced in a reproducible manner, to industrial quality levels, with dimensional accuracies of a hundredth of a millimeter. Furthermore, the surgeon must be able to prepare precise implant seats in the bone region without applying much force.

The milling cutter according to the invention is one in which the milling teeth form an opening in the surface of a milling body, this opening being formed from at least one cutting tongue, two gaps, two lateral boundaries and a reference edge, the reference edge having the length 1b being arranged opposite the cutter and having a shorter length than the total of the length 1s of the cutter and the width 1z of the gaps.

The milling cutter according to the invention is an accurate tool which not only facilitates the work of the surgeon but also considerably enhances the quality of intervention which can be achieved.

DESCRIPTION OF THE PREFERRED EMBODIMENTS

Figure 1:
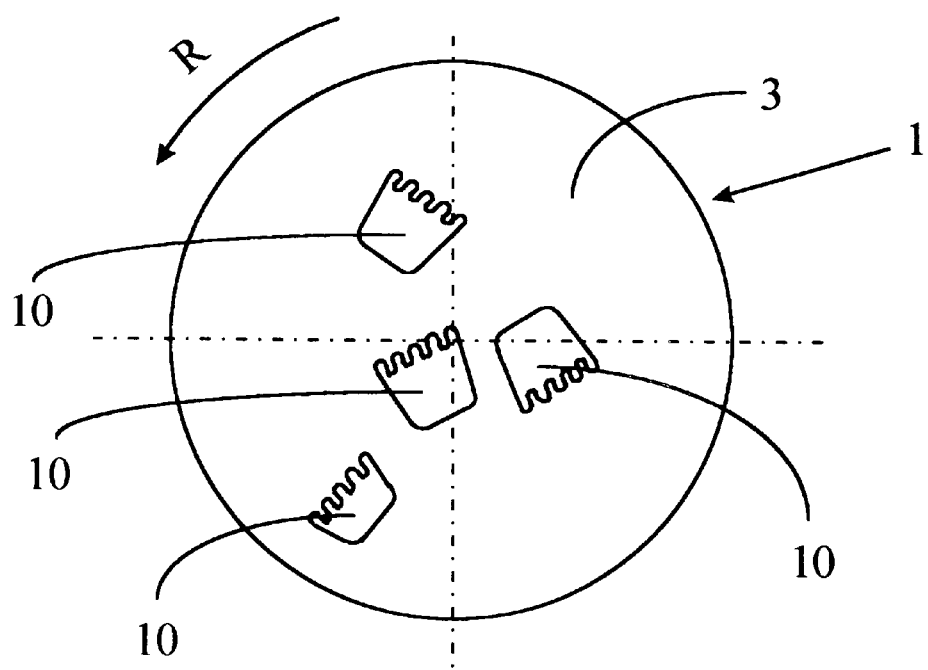
FIG. 1 shows a plan view of a milling cutter according to the invention.
Figure 2:
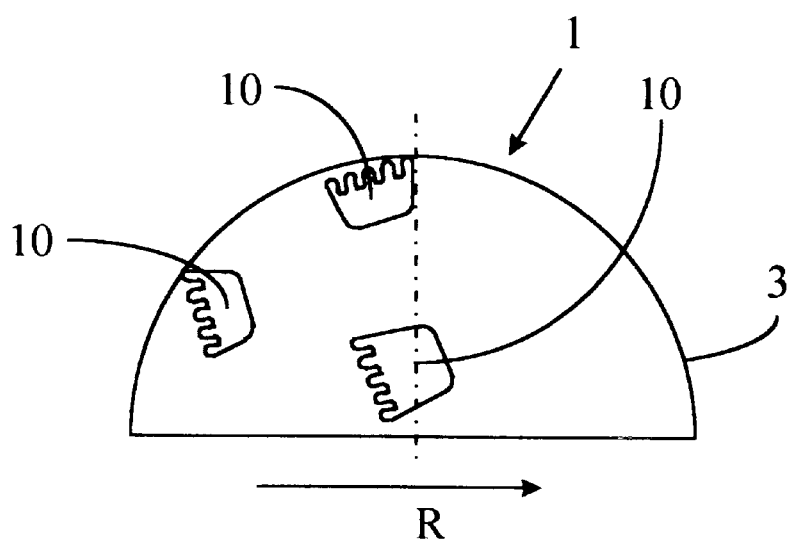
FIG. 2 shows a side view of a milling cutter according to the invention.

A possible embodiment of the milling cutter 1 according to the invention is shown, for example, by FIG. 1 and FIG. 2. The milling cutter 1 must be able to produce an implant seat of uniform shape out of the bone region. This can only be achieved, for example in the case of an acetabulum grating milling cutter if the milling body 2 is a dimensionally accurate hemisphere, the milling teeth or aperture 10 are arranged at the correct location in the milling body 2 and if these teeth have uniform dimensions and cut correctly.

To allow the milling body 2 to retain the shape imparted to it by deep-drawing or pressing, it must not be deformed further during any of the subsequent operations. This is achieved in accordance with the invention by selecting the shape of a milling tooth 10 in such a manner that mechanical production methods can be employed and the positions of the milling teeth can be defined using CAD and CAM engineering methods. The milling teeth 10 can thus be produced in the milling body 2 by the machine without first being drawn on. Modern cutting methods allow this without any problems using modern CIM and CAM engineering.

The accurate definition of the position of the milling teeth 10 on the milling body 2 allows the number of milling teeth 10 required to be optimized. It is clear that the risk of deformation to the milling body 2 is reduced as the number of milling teeth to be formed decreases. Moreover, a large number of milling teeth 10 impair the stability of the milling body 2. For these reasons, it is desirable to have to apply as few milling teeth 10 as possible to the milling body 2. On the other hand, it is only possible to reduce the number of milling teeth 10 if their dimensions are accurate and reproducible, so that their cutting performance is predictable.

Production takes place in three operations. In the first operation, the blanks made from sheet metal are given the desired shape of the milling body 2 by means of deep-drawing or pressing. Then, in the second operation, the substantially non-elongated cut outs or openings 15, with a dimensionally accurate reference edge 11 and sharp cutter 13 with sharp cutting edge 18, are formed on the dimensionally accurate milling body 2 using a computer-controlled machine. This is done using modern methods of cutting and production engineering. There are no problems with upsetting and deformation of the milling body 11, and even materials which are difficult to machine can be machined with the required accuracy. In a third operation, the cutting tongue 13 is bent up through angle α about the bending edge a, so that the cutter 12 is brought into the correct position. In many cases, this operation will be carried out manually.

In order to facilitate this manual operation, the shape of the opening 15 is to be defined in such a manner that it can serve as a guide for a tool 20a. To this end, the entire shape or individual elements of the opening 15 are defined, dimensioned and machined. It can be defined, for example, by cutting tongue 13, gaps 14, lateral boundaries 16 and the reference edge 11 situated opposite the cutting tongue 13. The requisite guidance for a tool 20a can also be achieved, for example, by precise definition of the reference edge 11 and the gaps 14. This method has the advantage that cutting tongue 13 and lateral boundaries 16 can be configured more freely. This can result in advantages for chip removal through the opening 15 which is also a function which the latter has to perform in use.

In production, the opening 15, or elements thereof, serves as template and guide for the tool part 20a. In any event, the reference edge 11 serves to position the bending edge a. These two elements are defined by distance and position in dependence on one another. If the tool part 20a for bending the cutting tongues 13 upward bears against the reference edge 11, the line a will automatically come to lie in the desired position with respect to the reference edge 11. The lateral guidance of the tool part 20a is defined either by the gaps 14, the lateral boundaries 16 or the side edges 17 of the cutting tongues 13.

Figure 4:
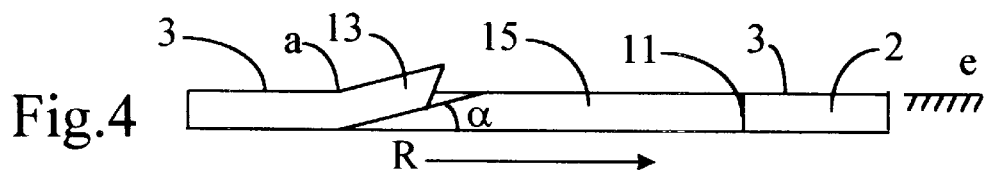
FIG. 4 shows a sectional view through a milling tooth on line A—A.
Figure 5:
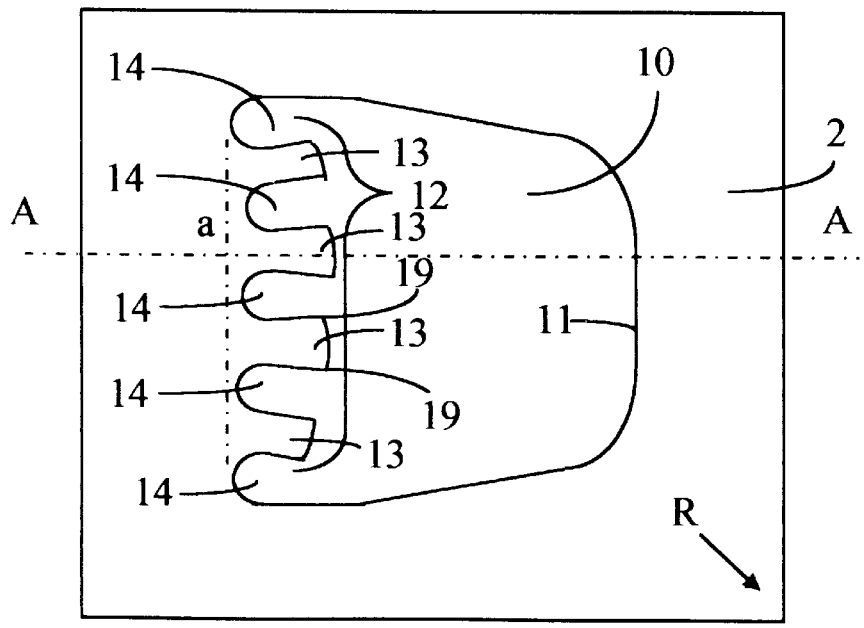
FIG. 5 shows a plan view of a milling tooth.
Figure 6:
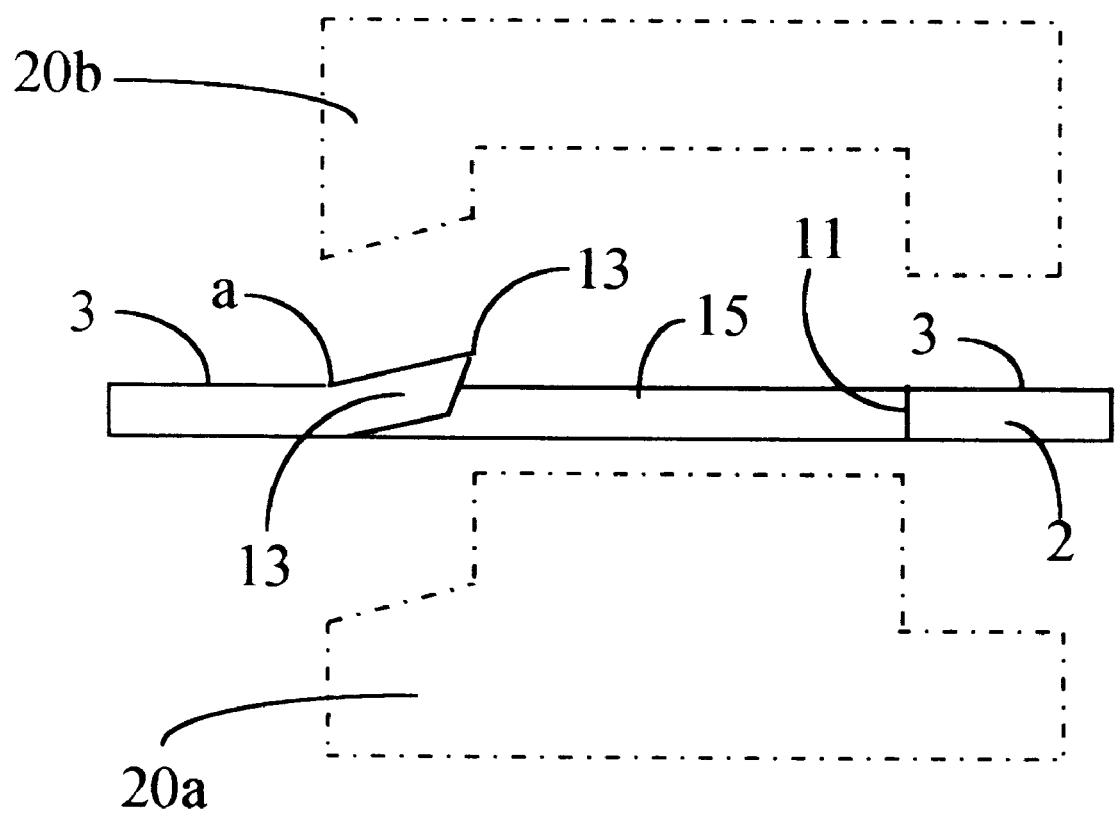
FIG. 6 shows a sectional view through a milling tooth on line A—A, with tools.

The milling body 2 will now come to lie over the lower part of a tool 20a, perpendicular to the plane e of the milling tooth 10 (cf. FIG. 4). In this position, the upper tool part 20b is pressed downward manually or using a machine. When pressed together, the two tool parts 20a and 20b bring the cutting tongue 13 into the desired position.

Such milling teeth 10 can be arranged in any desired shapes of milling bodies 2. If the milling teeth 10 are made in a flat metal sheet as milling body 2, the result is a type of file or rasp, with which any desired shapes can be produced. Such milling cutters are used, for example, to shape a bone extremity. The spherical shape of the milling body 2 is described above and is used primarily for preparing the implant seat for hip-joint prostheses. Cylindrical milling bodies 2 may serve, for example, to prepare the implant seat in the femur for hip prostheses. Like the spherical socket, which has to be held in the pelvis, the prosthesis shank which is fitted into the femur also has to be seated securely. In this application too, the quality of the seat is dependent on the quality of the tool used.

Figure 3:
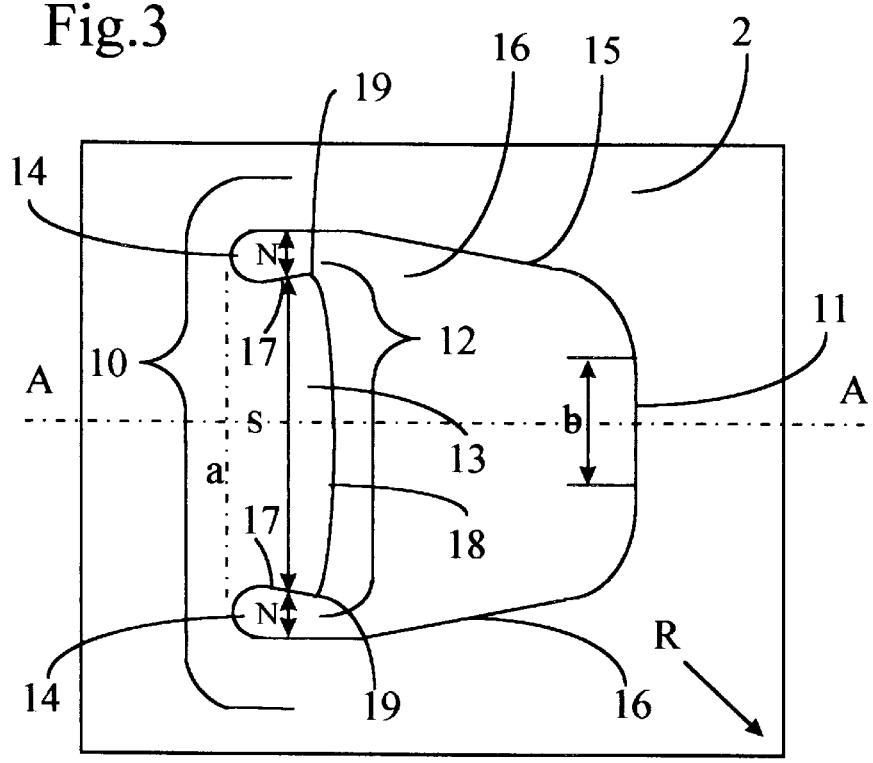
FIG. 3 shows a plan view of a milling tooth.

The shape of the cutter 12 plays an important role in these applications. As shown in FIG. 1, it may be formed from a cutting tongue 13. FIG. 3 shows the possibility of a plurality of cutting tongues 13 forming the cutter 12. A particular effect is achieved by the fact that in use the milling tooth 10 is moved in a direction R which deviates from the axis A—A, as shown in FIG. 3. In this case, the corner 19, lying in the direction of movement R, of a milling tooth 10 comes into engagement first.

Which elements of the cutting tongue 13 form the cutter 12 is important. It is obvious that the cutting edge 18 should be sharpened, so that only this cutting edge 18 forms the cutter 12. This may be sufficient for simple milling cutters 1 which are moved primarily in the direction of the axis A—A. In many other cases, it is important that the cutter 12 is formed not only by the cutting edge 18, but also that the side edges 17 and the corners 19 of the cutting tongues are sharpened, so that side edges 17, cutting edges 18 and corners 19 together form the cutter 12.

I claim:

1. A milling cutter (1) for use in orthopedic operations, comprising a milling body (2) made of thin-walled material, having a predetermined shaped and on its surface (3) having milling teeth (10) systematically assigned in terms of number and position to the milling cutter size and milling cutter shape, the arrangement and shape of the milling teeth (10) being defined with a predetermined level of accuracy, wherein the milling teeth (10) form a cut out (15) in the surface (3) of a milling body (2) wherein said cut outs each have an opposite side and have a shape and contour defined (a) by at least one cutting tongue (13) directed towards the opposite side of the cut out and slightly bent up relatively to the wall; (b) by two lateral boundaries (16); (c) by two gaps (14) between the cutting tongue and said lateral boundaries and (d) by a reference edge (11) opposite to the cutting tongue, the length of said reference edge being smaller than the total of the width of the cutting tongue and the width of the gaps, and, thus, smaller than the distance between the lateral boundaries.

2. The milling cutter for medical purposes as claimed in claim 1, wherein the milling cutter body 2 is a planar metal sheet.

3. The milling cutter for medical purposes as claimed in claim 1, wherein the milling body 2 has a spherical form.

4. The milling cutter for medical purposes as claimed in claim 1, wherein the milling body 2 has a cylindrical form.

5. The milling cutter for medical purposes as claimed in claim 1, wherein the milling body 2 has any desired three-dimensional form.

6. The milling cutter for medical purposes as claimed in claim 1, wherein a cutter (12) is formed by a cutting edge (18) of the cutting tongue (13).

7. The milling cutter for medical purposes as claimed in claim 1, wherein a cutter (12) is formed by cutting edge (18) and side edges (17).

8. A milling cutter (1) for use in orthopedic operations comprising a milling body (2) made of thin-walled material, having a predetermined shape and in its surface (3) having milling teeth (10) each having a location and defining a cutter size and a cutter shape, the milling teeth (10) systematically assigned in terms of number and position to the milling cutter size and milling cutter shape, the location, cutter size and shape being defined with a predetermined level of accuracy, wherein each milling tooth (10) forms a substantially non-elongated cut out (15) in the surface (3) of a milling body (2), wherein, said cut outs each have an opposite side and have a shape and contour defined (a) by at least one cutting tongue (13) directed towards the opposite side of the cut out and slightly bent up relatively to the wall; (b) by two lateral boundaries (16); (c) by two gaps (14) between the cutting tongue and said lateral boundaries and (d) by a reference edge (11) opposite to the cutting tongue, the length of said reference edge being smaller than the total of the width of the cutting tongue and the width of the gaps, and, thus, smaller than the distance between the lateral boundaries.

9. A milling cutter for use in orthopedic operations comprising a milling body made of thin-walled material, having a predetermined shape and in its surface having milling apertures each having a location and defining a cutter size and a cutter shape, the milling apertures systematically assigned in terms of number and position to the milling cutter size and milling cutter shape, the location, cutter size and shape being defined with a predetermined level of accuracy, wherein each milling aperture forms a substantially non-elongated cut out in the surface of a milling body wherein said cut outs each have an opposite side and have a shape and contour defined (a) by at least one cutting tongue directed towards the opposite side of the cut out and slightly bent up relatively to the wall;

(b) by two lateral boundaries;

(c) by two caps between the cutting tongue and said lateral boundaries and (d) by a reference edge opposite to the cutting tongue, the length of said reference edge being smaller than the total of the width of the cutting tongue and the width of the gaps, and, thus, smaller than the distance between the lateral boundaries.

* * * * *

UNITED STATES PATENT AND TRADEMARK OFFICE
CERTIFICATE OF CORRECTION

PATENT NO. : 5,968,049
DATED : OCTOBER 19, 1999
INVENTOR(S) : Da Rold

It is certified that error appears in the above-identified patent and that said Letters Patent is hereby corrected as shown below:

Column 4, line 31, replace   shaped   by --shape--

Column 6, line 13, replace   caps   by --gaps--

Signed and Sealed this

Twenty-first Day of November, 2000

Attest:

Q. TODD DICKINSON

Attesting Officer        Director of Patents and Trademarks